United States Patent
Bauer et al.

(10) Patent No.: US 10,202,554 B2
(45) Date of Patent: Feb. 12, 2019

(54) PROCESS AND PLANT FOR THE RECOVERY AND UTILIZATION OF HIGHER OLEFINS IN THE OLEFIN SYNTHESIS FROM OXYGENATES

(71) Applicant: L'Air Liquide, Societe Anonyme pour l'Etude et l'Exploitation des Procedes Georges Claude, Paris (FR)

(72) Inventors: Ingo Bauer, Bad Vilbel (DE); Martin Rothaemel, Frankfurt am Main (DE)

(73) Assignee: L'Air Liquide Societe Anonyme Pour L'Etude Et L'Exploitation Des Procedes Georges Claude, Paris (FR)

( * ) Notice: Subject to any disclaimer, the term of this patent is extended or adjusted under 35 U.S.C. 154(b) by 0 days.

(21) Appl. No.: 15/738,022

(22) PCT Filed: Jun. 10, 2016

(86) PCT No.: PCT/EP2016/025057
§ 371 (c)(1),
(2) Date: Dec. 19, 2017

(87) PCT Pub. No.: WO2016/202464
PCT Pub. Date: Dec. 22, 2016

(65) Prior Publication Data
US 2018/0305626 A1 Oct. 25, 2018

(30) Foreign Application Priority Data
Jun. 19, 2015 (EP) .................................... 15400024

(51) Int. Cl.
*C10G 7/00* (2006.01)
*C10G 69/12* (2006.01)
*C10G 45/44* (2006.01)

(52) U.S. Cl.
CPC ............. *C10G 69/123* (2013.01); *C10G 7/00* (2013.01); *C10G 45/44* (2013.01);
(Continued)

(58) Field of Classification Search
CPC ........... C07C 1/20; C07C 15/02; C07C 11/02; C07C 11/06; C07C 43/046; C07C 2/864;
(Continued)

(56) References Cited

U.S. PATENT DOCUMENTS

| 4,482,772 A | 11/1984 | Tabak |
| 4,543,435 A | 9/1985 | Gould et al. |

(Continued)

FOREIGN PATENT DOCUMENTS

| CN | 103 772 109 | 5/2014 |
| DE | 10 2005 048931 | 4/2007 |

(Continued)

OTHER PUBLICATIONS

International Search Report and Written Opinion for PCT/EP2016/025057, dated Aug. 23, 2016.

*Primary Examiner* — Sharon Pregler
(74) *Attorney, Agent, or Firm* — Justin K. Murray

(57) ABSTRACT

A process and a plant for producing olefins from oxygenates such as methanol and/or dimethyl ether are proposed, in which initially the oxygenates are converted to a primary product containing propylene, other olefins, paraffins and aromatics in an olefin synthesis reactor. The primary product is separated into hydrocarbon fractions of different C chain length, wherein short-chain olefins such as propylene are obtained and beside further fractions there is also obtained a $C_{7-}$ fraction which contains $C_5/C_6$ olefins, as well as a $C_{7+}$ fraction which contains aromatics. From the latter, the aromatics are separated and alkylated with the $C_5/C_6$ olefins to obtain alkyl aromatics. The same are hydrogenated completely and recirculated to the olefin synthesis reactor, where they likewise are converted to short-chain olefins.

14 Claims, 2 Drawing Sheets

Invention

(52) U.S. Cl.
CPC ............... *C10G 2300/1081* (2013.01); *C10G 2300/1088* (2013.01); *C10G 2400/22* (2013.01)

(58) Field of Classification Search
CPC .. C07C 15/04; C07C 7/08; C07C 2/66; C07C 13/12; C07C 5/11; B01D 15/00; B01D 2257/80; C10L 1/04; C10L 2200/0469; C10L 2270/023; C10L 2290/543
See application file for complete search history.

(56) References Cited

U.S. PATENT DOCUMENTS

2004/0039239 A1  2/2004  Shutt
2007/0284284 A1  12/2007  Zones et al.

FOREIGN PATENT DOCUMENTS

| | | | |
|---|---|---|---|
| DE | 10 2013 101578 | 8/2014 | |
| WO | WO 2006 136433 | 12/2006 | |
| WO | WO 2011 131647 | 10/2011 | |
| WO | WO 2014 124844 | 8/2014 | |
| WO | WO-2014124844 A1 * | 8/2014 | ............... C07C 1/20 |

* cited by examiner

PROCESS AND PLANT FOR THE RECOVERY AND UTILIZATION OF HIGHER OLEFINS IN THE OLEFIN SYNTHESIS FROM OXYGENATES

CROSS REFERENCE TO RELATED APPLICATIONS

This application is a § 371 of International PCT Application PCT/EP2016/025057, filed Jun. 10, 2016, which claims the benefit of EP15400024.4, filed Jun. 19, 2015, both of which are herein incorporated by reference in their entireties.

FIELD OF THE INVENTION

The present invention relates to a process for producing olefins from oxygenates, with the following steps:
(a) heterogeneously catalyzed conversion of an educt mixture comprising steam and oxygenates, such as methanol and/or dimethyl ether, under oxygenate conversion conditions in an olefin synthesis reactor to a primary product containing propylene, other olefins, paraffins and aromatics,
(b) separation of the primary product by means of physical separation processes into a $C_{5-}$ fraction, a $C_{5+}$ fraction and an aqueous phase containing non-converted oxygenates,
(c) separation of the $C_{5-}$ fraction by multistage distillation, wherein a propylene product stream and several olefin-containing hydrocarbon fractions are obtained, wherein the latter are at least partly recirculated to the olefin synthesis reactor,
(d) separation of the non-converted oxygenates from the aqueous phase by means of a thermal separation process, recirculation of the separated, non-converted oxygenates and at least a part of the water to the olefin synthesis reactor, and
(e) separation of the $C_{5+}$ fraction by multistage distillation, wherein a $C_{7-}$ fraction is obtained which comprises $C_5/C_6$ olefins, and wherein a $C_{7+}$ fraction is obtained which comprises aromatics.

Furthermore, certain embodiments of the invention can include a plant for carrying out this process.

BACKGROUND OF THE INVENTION

Propene ($C_3H_6$), often also referred to as propylene, is one of the most important starting substances of the chemical industry. The demand for the base material propylene is increasing worldwide, wherein propylene just like ethylene mostly is produced from petroleum in a steam cracker in a ratio dependent on the process conditions and the raw materials.

To obtain additional propylene, a number of processes exist, such as the propane dehydrogenation which proceeds from propane as educt. What is known, however, above all is the so-called MTP (Methanol-to-Propylene) process, in which so-called oxygenates such as methanol (MeOH) or dimethyl ether (DME) are converted to olefins by catalytic conversion on a zeolitic catalyst. By varying the catalyst and the process conditions, the selectivity of the products obtained can be influenced and the product spectrum thus can be shifted towards short-chain olefins (then often also the process name Methanol-to-Olefin (MTO)), towards longer-chain products (then often also the process name Methanol-to-Gasoline (MTG)) or towards propylene.

The fundamentals of an MTP process are described for example in the document DE 10 2005 048 931 A1. From an educt mixture containing steam and oxygenates, such as methanol and/or dimethyl ether, $C_2$ to $C_4$ olefins are produced above all. By a heterogeneously catalyzed reaction in at least one reactor, the educt mixture is converted to a reaction mixture comprising low-molecular olefins and gasoline hydrocarbons. By a suitable separation concept, higher olefins, above all the $C_{5+}$ fraction, can at least partly be recirculated into the reactor as recycling stream and in said reactor for the most part be converted to propylene, whereby the yield of propylene is increased.

The MTP process usually has a propylene yield of about 65% (mole C). An increased propylene yield would distinctly improve the economy of the process. As predominant by-product in the MTP process a gasoline-like mixture (MTP gasoline) is obtained, which substantially consists of olefins, paraffins, cyclic hydrocarbons and aromatics. This MTP gasoline likewise can be incorporated into a succeeding value chain, but has a lower market price than propylene.

As described in the document WO 2006/136433 A1 it therefore is attempted for example to subject the MTP gasoline or fractions of the same to a post-processing in the form of an olefin metathesis, in which the MTP gasoline or fractions obtained therefrom is converted on a zeolitic catalyst at temperatures of about 400 to 500° C. and a pressure of 1 to 5 bar. Due to this downstream reaction, a moderate increase of the propylene yield of the entire process can be achieved, but the total yield still lies below 70 mol-%.

A direct recirculation of the MTP gasoline into the MTP reactor provides no increase in the yield of propylene. Since undesired alkylation reactions of the aromatics occur inside the MTP reactor, which consume methanol which then no longer is available for the selective formation of propylene, the propylene yield of the entire process even would decrease in the case of the direct recirculation of the MTP gasoline into the MTP reactor.

Some processes therefore aim at converting the heavier olefins obtained, so that at least a product with homogeneous composition and higher market price is obtained. The patent specification U.S. Pat. No. 4,543,435 for example teaches that at least a part of the olefins obtained is to be converted to heavy hydrocarbons, so that the yield of liquefied gas and gasoline can be increased within the MTP process.

WO 2011/131647 describes a process for producing aromatic hydrocarbons, in which a feed of light alkanes is at least partly converted to aromatics on a suitable catalyst. Parallel thereto an MTO process takes place. A part of the oxygenate feed of the MTO process is produced in that the hydrogen obtained during the conversion of the alkanes to aromatics is converted to an oxygenate with carbon monoxide and/or carbon dioxide. The product streams thus obtained can easily be combined with the other by-products of the MTP process, above all methane, carbon oxides, hydrogen and a product similar to liquefied gas.

For increasing the yield of valuable products from an MTP process, a hydrogenation of the aromatic hydrocarbons obtained also is known. US 2004/0039239 for example teaches that higher olefins are to be hydrogenated on a suitable hydrogenation catalyst. In particular due to the fact that aromatics also are hydrogenated to paraffins, the yield of a gasoline-like valuable product thus can be increased.

From the patent specification U.S. Pat. No. 4,482,772 a hydrogenation within an MTP process is known, in which first the conversion of the oxygenates to olefins takes place and the olefins thus obtained subsequently are oligomerized.

Subsequent to the oligomerization, at least parts of the product stream are hydrogenated, whereby aromatics contained in the product stream are converted to cycloparaffins. The yield of a gasoline-like valuable product likewise can be increased thereby.

For carrying out such hydrogenations, various types of catalyst and their possible applications are known for example from the patent application US 2007/0284284 A1.

Finally, the International Patent Application WO 2014/124844 A1 proposes a modified MTP process in which an aromatics fraction is obtained and the same is converted into a fraction containing cycloparaffins by hydrogenation. The latter is recirculated to the olefin synthesis reactor as recycle stream and in said reactor partly converted to olefins, among them propylene. In this way an increase of the propylene yield is achieved already, but reactive components, in particular $C_{5+}$ olefins, still remain unused for the formation of propylene and for example are admixed to the MTP gasoline. Another part of the $C_{5+}$ olefins is withdrawn from the process via purge streams, whose actual task it is to prevent an enrichment of the $C_{5+}$ paraffins in the MTP process.

SUMMARY OF THE INVENTION

Against this background it is the object of certain embodiments of the present invention to provide a process in which the propylene yield can be increased distinctly by improved utilization and recirculation of the by-products of the olefin synthesis reaction from oxygenates, in particular the $C_{5+}$ olefins and the aromatics.

This object can be solved by a process and by a plant with the features of the various embodiments described herein.
Process According to the Invention:

In one embodiment, a process for producing olefins, in particular propylene, from oxygenates, can include the following steps:
 (a) heterogeneously catalyzed conversion of an educt mixture comprising steam and oxygenates, such as methanol and/or dimethyl ether, under oxygenate conversion conditions in an olefin synthesis reactor to a primary product containing propylene, other olefins, paraffins and aromatics,
 (b) separation of the primary product by means of physical separation processes into a $C_{5-}$ fraction, a $C_{5+}$ fraction and an aqueous phase containing non-converted oxygenates,
 (c) separation of the $C_{5-}$ fraction by multistage distillation, wherein a propylene product stream and several olefin-containing hydrocarbon fractions are obtained, wherein the latter are at least partly recirculated to the olefin synthesis reactor,
 (d) separation of the non-converted oxygenates from the aqueous phase by means of a thermal separation process, recirculation of the separated, non-converted oxygenates and at least a part of the water to the olefin synthesis reactor,
 (e) separation of the $C_{5+}$ fraction by a thermal separation process, wherein a $C_{7-}$ fraction is obtained which comprises $C_5/C_6$ olefins, and wherein a $C_{7+}$ fraction is obtained which comprises aromatics,
 (f) separation of the $C_{7+}$ fraction by a thermal separation process, preferably by extractive distillation into an aromatics fraction and a fraction comprising the $C_{7+}$ paraffins,
 (g) supplying at least a part of the $C_{7-}$ fraction comprising the $C_5/C_6$ olefins and at least a part of the aromatics fraction to an alkylation reactor in which by heterogeneously catalyzed conversion of the aromatics with the $C_5/C_6$ olefins on an alkylation catalyst under alkylation conditions an alkylation product is obtained, which comprises alkyl aromatics,
 (h) separation of the alkylation product by a thermal separation process in a stream containing $C_5/C_6$ paraffins, an alkyl aromatics stream and a stream containing non-converted aromatics, which is at least partly recirculated to the alkylation reactor,
 (i) supplying the alkyl aromatics stream to a hydrogenation reactor in which by heterogeneously catalyzed conversion of the alkyl aromatics on a hydrogenation catalyst under hydrogenation conditions a hydrogenation product is obtained, which comprises cycloparaffins, and (g) recirculation of at least a part of the hydrogenation product to the olefin synthesis reactor.

Plant According to the Invention:

In another embodiment, a plant for producing olefins from oxygenates, in particular for carrying out the process according to any of the preceding claims, can include the following plant sections which are in fluid connection with each other:
 at least one olefin synthesis reactor for the heterogeneously catalyzed conversion of at least one oxygenate to a primary product containing propylene, other olefins, paraffins and aromatics,
 a separating device for separating the primary product into a $C_{5-}$ fraction, a $C_{5+}$ fraction and an aqueous phase containing non-converted oxygenates,
 a separating device for separating the $C_{5-}$ fraction into a propylene product stream and several olefin-containing hydrocarbon fractions, as well as return conduits for recirculating at least a part of the olefin-containing hydrocarbon fractions to the olefin synthesis reactor,
 a separating device for separating the non-converted oxygenates from the aqueous phase, as well as return conduits for recirculating at least a part of the non-converted oxygenates and at least a part of the water to the olefin synthesis reactor,
 a separating device for separating the $C_{5+}$ fraction into a $C_{7-}$ fraction which comprises $C_5/C_6$ olefins, and into a $C_{7+}$ fraction which comprises aromatics,
 a separating device for separating the $C_{7+}$ fraction into an aromatics fraction and a fraction comprising the $C_{7+}$ paraffins,
 an alkylation reactor for the heterogeneously catalyzed conversion of aromatics with $C_5/C_6$ olefins to an alkylation product which comprises alkyl aromatics, as well as conduits for supplying at least a part of the $C_{7-}$ fraction comprising the $C_5/C_6$ olefins and at least a part of the aromatics fraction to the alkylation reactor,
 a separating device for separating the alkylation product into a stream containing $C_5/C_6$ paraffins, an alkyl aromatics stream and a stream containing non-converted aromatics, as well as a return conduit for recirculating at least a part of the stream containing non-converted aromatics to the alkylation reactor,
 a hydrogenation reactor for hydrogenating the alkyl aromatics to a hydrogenation product which comprises cycloparaffins,
 a return conduit for recirculating at least a part of the hydrogenation product to the olefin synthesis reactor.

The oxygenate conversion conditions required for the conversion of oxygenates to olefin products, the alkylation conditions required for the alkylation of aromatics with olefins, and the hydrogenation conditions required for the hydrogenation of alkyl aromatics to cycloparaffins are known to the skilled person from the prior art, for example from the documents discussed above. Necessary adaptations of these conditions to the respective operating requirements will be made on the basis of routine experiments. The specific reaction conditions disclosed below can serve as orientation, but are not to be understood in a limiting sense with respect to the scope of the invention.

Thermal separation processes in the sense of the invention include all separation processes which are based on obtaining a thermodynamic phase equilibrium. The distillation or rectification is preferred. In principle, however, the use of other thermal separation processes also is conceivable, for example the extraction or extractive distillation.

Fluid connection between two regions or plant sections is understood to be any kind of connection which enables a fluid, for example a reaction product or a hydrocarbon fraction, to flow from the one to the other of the two regions, regardless of any interposed regions, components or necessary conveying means.

Oxygenates in principle are understood to be all oxygen-containing hydrocarbon compounds which under oxygenate conversion conditions can be converted to olefins, in particular to short-chain olefins such as propylene, and further hydrocarbon products.

Short-chain olefins in accordance with the present invention in particular are understood to be olefins which under ambient conditions are present in gaseous form, for example ethylene, propylene as well as the isomeric butenes 1-butene, cis-2-butene, trans-2-butene, iso-butene.

For designating hydrocarbon fractions the following nomenclature is used: "$C_n$ fraction" designates a hydrocarbon fraction which chiefly contains hydrocarbons of the C chain length n, i.e. with n C atoms. "$C_{n-}$ fraction" designates a hydrocarbon fraction which contains hydrocarbons of the C chain length n and with lower C chain lengths. "$C_{n+}$ fraction" designates a hydrocarbon fraction which contains hydrocarbons of the C chain length n and with higher C chain lengths. Due to the physical separation processes used, for example the distillation, the separation with regard to the C chain length is not to be understood such that hydrocarbons with another chain length are rigorously excluded. For example, depending on the process conditions of the separation process a $C_{n-}$ fraction still contains small amounts of hydrocarbons with a C number greater than n.

The invention is based on the finding that $C_5/C_6$ olefins can be separated from the $C_{7-}$ fraction in an efficient and selective way by converting the same to alkyl aromatics with an aromatics fraction inherent to the process. The advantage is that the entire process does not lose any olefins which can at least partly be converted to the target product propylene by recirculation.

In a succeeding step, the alkyl aromatics obtained are hydrogenated to cycloparaffins, substantially to cyclohexane derivatives with alkyl side chain. The hydrogenation is necessary as otherwise the aromatics would undesirably be alkylated by methanol during recirculation to the olefin synthesis reactor. The cycloparaffins thus obtained can then be recirculated into the heterogeneously catalyzed olefin synthesis, where they are converted in a known way to olefins with a shorter chain length, in particular to propylene, without undesired alkylation reactions occurring, since the cycloparaffins already exactly correspond to olefins in terms of their empirical chemical formula ($C_nH_{2n}$). After ring opening, the conversion is effected with moderate turnover, but good selectivity to ethylene, propylene and higher olefins.

BRIEF DESCRIPTION OF THE DRAWINGS

Further features, advantages and possible applications of the invention can also be taken from the following description of exemplary embodiments and numerical examples as well as the drawings. All features described and/or illustrated form the subject-matter of the invention per se or in any combination, independent of their inclusion in the claims or their back-reference.

In the drawings.

DETAILED DESCRIPTION OF THE INVENTION

Figure 1:
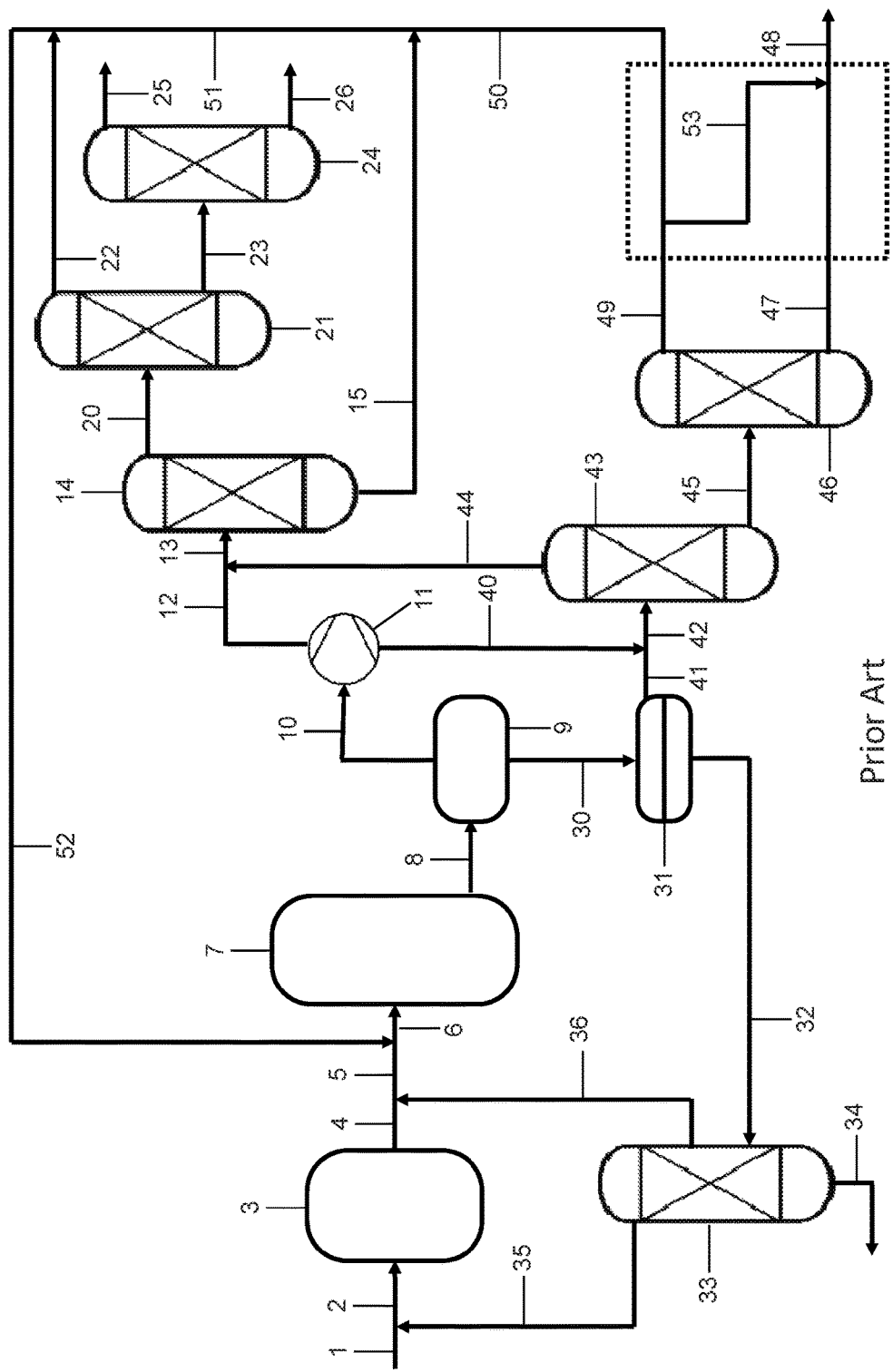
FIG. 1 shows the schematic representation of an MTP process and a corresponding plant according to the prior art.

For the hydrogenation reaction, hydrogen ($H_2$) advantageously is used as hydrogenating agent. Since the aromatics and cyclic olefins originate from the MTP reaction, they include no inorganic catalyst poisons such as sulfur etc. Thus, very moderate conditions at temperatures of less than 150° C. and pressures of less than 25 bar can be used for the hydrogenation, in order to achieve an almost complete conversion. There can be used standard hydrogenation catalysts, which contain e.g. nickel or palladium as active component which is applied on a carrier, e.g. activated carbon.

It also was found to be advantageous that the hydrogenation is carried out such that parts of the product stream of the hydrogenation are recirculated into the hydrogenation, and that the ratio between the recirculated hydrogenated product and non-hydrogenated alkyl aromatics lies between 1 kg/kg and 10 kg/kg. By setting this ratio, a dilution of the educts to be converted can be achieved. This is necessary because the hydrogenation is a strongly exothermal reaction and otherwise too strong heating of the reaction mixture occurs within the hydrogenation. The use of hydrogenated product as diluent has the advantage that in this way no further components are introduced into the process. In the hydrogenated product a distinction must be made between liquid product streams and gaseous product streams, which substantially consist of non-converted hydrogen and formed light gases. Due to the greater density it is advantageous to use the liquid product for diluting the hydrogenation.

The molar excess of hydrogen should lie between 200 and 5000% of the quantity theoretically necessary for the complete saturation of all existing double and aromatic bonds. Thus, a limitation of the reaction due to limited local hydrogen concentrations can completely be excluded.

By separating hydrogen after the hydrogenation, the excess of hydrogen is irrelevant for the further processing of the hydrogenated stream, and the non-converted hydrogen also can be recirculated into the hydrogenation, so that actually no increased hydrogen consumption occurs. Correspondingly, only the stoichiometrically necessary quantity of hydrogen must be added continuously. An enrichment of gaseous by-products of the hydrogenation, such as e.g. methane, can be controlled in that a continuous small purge stream is removed from the process part.

Furthermore, it was found to be advantageous to separate a $C_5$ fraction from the remaining residual stream already after the heterogeneously catalyzed olefin synthesis. Thus, the particularly valuable low-molecular olefins, in particular the propylene itself, can immediately be withdrawn from the product stream of the heterogeneously catalyzed conversion, which is why all succeeding plant components for the processing of the higher olefins can be dimensioned smaller.

The separation advantageously is effected by cooling, in which the $C_5$ fraction remains gaseous and due to its state of matter separates from the remaining liquid residual stream. The energy thus gained can be utilized at another point in the process.

From the remaining residual stream an aqueous fraction containing oxygenates is obtained on the one hand, and on the other hand a $C_{5+}$ fraction. Preferably, this is achieved by a simple phase separation, whereby high energy costs, as they are incurred for example by a distillation, can be saved.

Advantageously, the aqueous fraction containing oxygenates is subjected to a separation process, in which the oxygenates, i.e. in essence methanol and/or dimethyl ether and the water are separated from each other. This separation preferably is effected in a distillation, in order to ensure sufficient separation sharpness. At least parts of the water are discharged from the process. Separated methanol and/or separated water can be recirculated into the heterogeneously catalyzed olefin synthesis. The recirculation of the water preferably is effected as steam.

In a particularly preferred configuration of the entire process the olefin synthesis is effected in two stages, wherein in the first stage the at least one oxygenate first is converted to at least one corresponding ether and in the second stage the ether(s) is/are converted to olefins. When methanol is used as oxygenate, a conversion of the methanol to dimethyl ether first is effected and subsequently the conversion of the dimethyl ether to propylene and other olefins, in particular also to aromatics. In this two-stage configuration it is recommendable to recirculate methanol already to before the first stage, i.e. before the conversion to dimethyl ether, while the vaporous water is introduced between the first and the second stage, as it must first be used as educt for the conversion of the ether to olefins. Thus, in the first stage no unnecessary water is used, which negatively influences the equilibrium reaction during the etherification; the steam however is available as educt in the olefin synthesis.

The product from the oxygenate conversion reaction initially is cooled by means of methods known to the skilled person, wherein water and water-soluble components such as oxygenates (methanol, DME) are condensed out and thus can easily be separated from the remaining hydrocarbon product. The resulting aqueous stream then is supplied to a suitable separating means (e.g. a distillation column), wherein the oxygenates are recirculated into the first reaction stage, as described above. The amount of water resulting from the conversion of the oxygenates is removed from the process, while the residual amount is recirculated to before the second reaction stage, as described above, so that closed circuits are obtained for the most part.

The largely water-free hydrocarbon stream is compressed after the cooling; there is obtained a pressurized light hydrocarbon stream and a liquid, likewise pressurized heavy hydrocarbon stream. To safely separate possibly still contained lighter olefins, it is recommendable to connect a further separation stage in which possibly still contained $C_{4-}$ fractions can be removed from the $C_{5+}$ fraction. Advantageously, this separation stage is a distillation, in order to ensure sufficient separation sharpness.

Preferably, at least parts of the $C_{7-}$ fraction comprising the $C_5/C_6$ olefins are recirculated to the olefin synthesis reactor. Due to the fact that not the entire $C_{7-}$ fraction is guided to the alkylation, the alkylation reactor and the succeeding hydrogenation reactor can be designed smaller. Thus, a compromise is achieved between lower investment costs, due to smaller apparatus sizes, and a moderate loss of $C_5/C_6$ olefins.

Furthermore, it was found to be advantageous when the separation of the $C_{7-}$ from the $C_{7+}$ fraction is effected out of the previously separated $C_{5+}$ fraction. This has the advantage that due to the early separation of the $C_{5-}$ fraction, the guided streams are distinctly smaller and the apparatus expenditure thus becomes smaller.

In a development of the invention it also is recommendable to supply at least a part of the stream obtained in process step (h), which contains non-converted aromatics, to the hydrogenation reactor. The yield of cycloparaffins can further be increased thereby and thus the recycle of convertible material to the olefin synthesis reactor can be increased.

It was found to be particularly advantageous that in the olefin synthesis reactor and in the alkylation reactor the same catalyst is used. Apart from logistic advantages this has the benefit that in the alkylation only such alkylation products largely are formed which are small enough to leave the pore system of the catalyst. This benefit is relevant in particular when using zeolite-based catalysts. Since the molecule size only changes insignificantly due to the succeeding hydrogenation, the alkylation products thus also can diffuse into the catalyst used in the olefin synthesis reactor and be converted there.

In process step (g), the ratio of the sum of the moles of aromatics in the aromatics-containing streams or fractions to the sum of the moles of olefins in the $C_{7-}$ fraction supplied to the alkylation reactor advantageously lies between 1 and 10 mol/mol, preferably between 1 and 5 mol/mol, most preferably between 1 and 2 mol/mol, so that it is ensured that a complete conversion of the olefins is possible stoichiometrically by alkylation with an aromatics molecule. An excess of the sum of aromatics to the sum of olefins in the feed to the alkylation reactor also ensures that undesired multiple alkylations only occur to a subordinate extent. These undesired multiple alkylations, however, also are minimized by the pore structure of the catalysts used (e.g. ZSM-5), as larger molecules cannot be formed at all within the pore structure.

In a particular configuration of the plant according to the invention, the same includes a return conduit for the recirculation of at least a part of the $C_{7-}$ fraction comprising the $C_5/C_6$ olefins to the olefin synthesis reactor. Due to the fact that not the entire $C_{7-}$ fraction is guided to the alkylation, the alkylation reactor and the succeeding hydrogenation reactor can be designed smaller. Thus, a compromise is achieved between lower investment costs, due to the smaller apparatus sizes, and a moderate loss of $C_5/C_6$ olefins.

It furthermore is advantageous when the plant also comprises a conduit for supplying at least a part of the stream containing the non-converted aromatics to the hydrogenation reactor. By supplying a part of the non-converted aromatics to the hydrogenation reactor, the yield of cycloparaffins can further be increased and thus the recycle of convertible material to the olefin synthesis reactor can be increased.

In a further aspect of the invention the plant also comprises return conduits for recirculating at least a part of the non-converted hydrogen and at least a part of the hydrogenation product to the hydrogenation reactor. By recirculating the hydrogenation product, a dilution of the educts to be converted can be achieved. This is necessary because the hydrogenation is a strongly exothermal reaction and otherwise too strong heating of the reaction mixture occurs within the hydrogenation. The use of hydrogenated product as diluent has the advantage that in this way no further components are introduced into the process. By recirculating non-converted hydrogen, the desired high excess of hydrogen in the hydrogenation reactor can be achieved, wherein only the actually stoichiometrically consumed hydrogen must newly be supplied as feed. Thus, a limitation of the reaction due to limited local hydrogen concentrations can be excluded completely.

The term "column" as used below basically relates to a distillation column, unless another thermal separation process is indicated in the individual case.

FIG. 1 shows an MTP process according to the prior art. Via conduits 1 and 2, methanol is introduced into a reactor 3 in which the methanol is at least partly converted to dimethyl ether. Via conduits 4, 5 and 6, the dimethyl ether is withdrawn and supplied to a second reactor 7, the olefin synthesis reactor, in which the dimethyl ether together with steam is converted to olefins. The olefin stream thus obtained contains propylene and other olefins, but also paraffins, cyclic olefins, cyclic paraffins and aromatics.

Via conduit 8, the product stream obtained is introduced into the cooling device 9. There, a gaseous phase separates from a liquid phase. The gaseous phase contains the $C_{5-}$ fraction and is supplied to a compressor 11 via conduit 10. The gaseous fraction obtained in the compressor 11 is supplied to a distillation column 14 via the conduits 12 and 13. In this distillation column 14, the $C_{3-}$ fraction is separated from the $C_{4+}$ fraction.

Via conduit 20, the $C_{3-}$ fraction is supplied to a column 21 in which the $C_{2-}$ fraction is withdrawn overhead. Via conduit 22 and conduit 52, the $C_{2-}$ fraction gets back into conduit 5 and from there can be guided via conduit 6 into the reactor 7, so that here the desired product propylene is at least partly produced by olefin metathesis. To avoid an enrichment of inert light gaseous components such as methane or carbon oxides in the circuit, a small partial quantity of the stream from conduit 22 can be removed from the system as purge stream (purge) via a non-illustrated conduit. Furthermore, the $C_3$ fraction is withdrawn from the column 21 via conduit 23 and supplied to a column 24. In this column 24, the desired target product propylene is distilled off overhead and withdrawn via conduit 25, while in the bottom propane is left and is withdrawn via conduit 26.

Via conduit 15, the bottom product of the column 14 is withdrawn from the column 14 as $C_4$ fraction, and via the conduits 51 and 52 it is likewise recirculated to before the conversion of the ether to olefins in conduit 5, in order to further increase the yield of propylene by olefin metathesis. To avoid an enrichment of butane (a component inert for the conversion in the reactor) in the circuit, a small partial quantity of the stream from conduit 15 can be removed from the system as purge via a non-illustrated conduit.

The liquid fraction obtained in the cooler 9 is supplied to a separator 31 via conduit 30. The aqueous phase separated in the separator 31 also contains oxygenates (when using methanol as educt, above all methanol, but also dimethyl ether) and is supplied to a distillation column 33 via conduit 32.

From the bottom of the column 33 water is discharged via conduit 34. Furthermore, steam is withdrawn from the column 33 via conduit 36 and fed into conduit 4, from where the steam gets into the reactor 7 via conduit 5 and conduit 6, in which reactor it is used as educt for the conversion of the dimethyl ether to olefins.

The top product of the column 33, at least one oxygenate, preferably methanol, is fed into the conduit 1 via conduit 35 and thus gets into the reactor 3 via conduit 2. The column 33 also can be configured as combination of several series-connected columns (not shown). When methanol is used as educt, recovered methanol together with the methanol fed in as educt thus is converted to dimethyl ether. Alternatively, the oxygenate also can directly be recirculated into the reactor 7 together with the steam via conduit 36. This is recommendable in particular when significant amounts of dimethyl ether also are present as oxygenate beside methanol.

The organic phase withdrawn from the separator contains the $C_{5+}$ fraction, which is discharged via conduit 41 and passed on via a pump (not shown). To this $C_{5+}$ fraction, the liquid fraction obtained from the compressor 11 at 15 to 25 bar then is also admixed via conduit 40. The combined streams then are introduced into a column 43 via conduit 42. From the head of the column 43, the $C_{4-}$ fraction is introduced via conduit 44 into the conduit 12, from where it is fed into the column 14 together with the gaseous part from the compressor 11 via conduit 13.

Via conduit 45, the bottom product of the column 43, which contains the $C_{5+}$ fraction, is guided into the column 46. From the bottom of the column 46, the $C_{7+}$ fraction is withdrawn into the conduits 47 and 48.

Over the head of the column 46, the $C_{7-}$ fraction obtained via conduits 49, 50, 51 and 52, which also comprises $C_5/C_6$ hydrocarbons, is recycled in that it is recirculated into the conduit 5. Parts of the $C_5$ and $C_6$ fraction are supplied to the conduit 47 via conduit 53 and discharged from the process via conduit 48 (purge). The stream leaving the process via conduit 48 represents the MTP gasoline.

Figure 2:
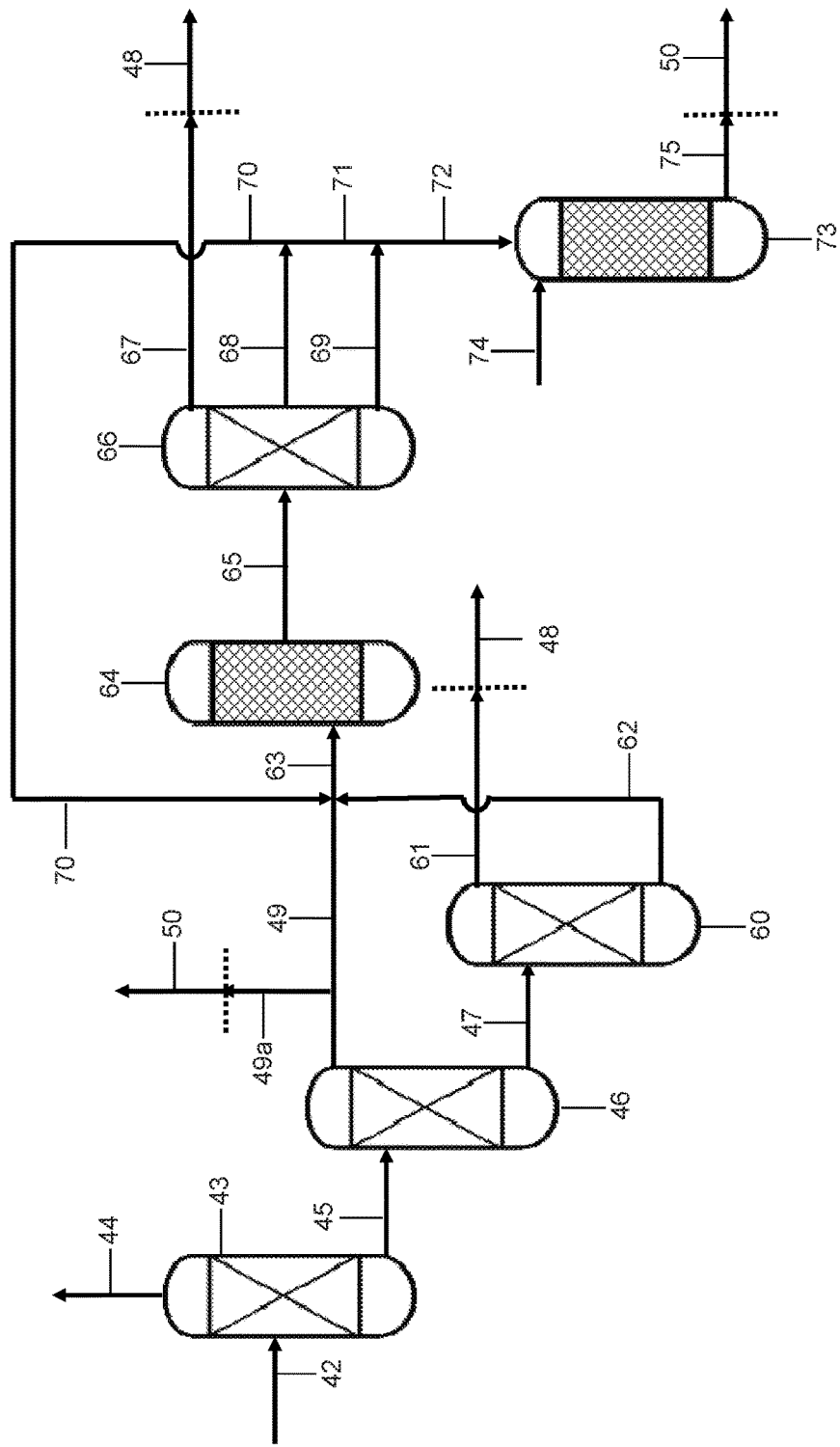
FIG. 2 shows the schematic representation of the process according to the invention or the plant according to the invention.

FIG. 2 schematically illustrates the procedure of the process according to the invention or the structure of a plant according to the invention. Up to the plant component 52, the process according to the invention or the plant according to the invention corresponds to the process already known from the prior art. The arrangement of the part between the conduits 47, 48, 49 and 50, which is modified according to the invention, is indicated in FIG. 1 by a dotted frame. The dotted lines shown in FIG. 2 correspondingly indicate points of connection to the basic process shown in FIG. 1. Conduit 53 is omitted in the process according to the invention or in the plant according to the invention.

Via conduit 47, the $C_{7+}$ fraction is introduced into a column 60. In an advantageous configuration, this column 60 is operated as extractive distillation and supplied with an additional stream which has advantageous chemical and physical properties, so that an even better separation between $C_{7+}$ olefins and paraffins in the head and aromatics in the bottom is possible. The stream used as extracting agent for example can be an olefin or a stream rich in aromatics, which preferably is produced and recirculated within the plant. However, external auxiliary substances such as N-methylpyrrolidone (NMP) can also be used. The operating principle is based on the fact that either the olefins in the head or the aromatics in the bottom are enriched.

At the head of the column 60, a fraction is discharged via conduit 61, which contains $C_{7+}$ olefins and -paraffins. This fraction is admixed to the MTP gasoline via conduit 48.

The aromatics fraction obtained in the bottom of column 60 is supplied to the alkylation reactor 64 via conduits 62 and 63, which reactor is designed as adiabatic fixed-bed reactor and in this exemplary embodiment is filled with the same catalyst as the olefin synthesis reactor, a commercially available zeolite catalyst of the structure type ZSM-5. However, other suitable alkylation catalysts can also be used, which are provided by the trade. Furthermore, the $C_{7-}$ fraction obtained at the head of the column 46, which also comprises $C_5/C_6$ olefins, also is supplied to the alkylation reactor. In the alkylation reactor the conversion of the $C_5/C_6$ olefins with the aromatics is effected at temperatures between 80 and 180° C. The pressure is chosen so high that the conversion is effected in the liquid phase; it lies between 1 and 20 bar, absolute. As alkylation products aromatics with $C_5$ and $C_6$ side chains are formed, wherein depending on the kind of starting aromatics the aromatic core either carries no further alkyl group (benzene), one further alkyl group (toluene) or several further alkyl groups (xylenes etc.). Multiple alkylations of the same aromatic core by several olefin molecules are undesirable, as the molecules obtained are too bulky and no longer can be converted easily in the olefin synthesis reactor, as they can diffuse into the pores of the catalyst used there only with difficulty. The formation of multiply alkylated products is suppressed further by setting a molar ratio of the aromatics in conduit 63 to the olefins in the same conduit of >1 mol/mol. In addition, their formation is reduced by the form-selectivity of the ZSM-5 zeolite also used as alkylation catalyst.

Via conduit 65 the product of the alkylation reactor, which beside alkyl aromatics also comprises non-converted starting aromatics and non-converted hydrocarbons, in particular paraffins, is supplied to the column 66. In the column 66, which also can comprise several series-connected columns, the distillative separation into a low-boiling fraction which comprises $C_5/C_6$ hydrocarbons, in particular the $C_5/C_6$ paraffins, and is admixed to the MTP gasoline via conduits 67 and 48, furthermore into a fraction boiling in the medium temperature range, which above all comprises non-converted starting aromatics and for one part is recirculated to the alkylation reactor 64 via conduits 68, 70 and 63 and for the other part is supplied to the hydrogenation reactor 73 via conduits 68, 71 and 72, and finally into a high-boiling fraction which comprises alkyl aromatics and likewise is supplied to the hydrogenation reactor 73 via conduits 69 and 72 is effected.

The hydrogenation reactor 73 for example can be a constructively simple fixed-bed reactor, but there can also be used reactors with internal cooling, of the single- or multistage type. As catalysts, there can be used for example nickel, palladium, platinum, further noble metals or mixtures thereof on carrier materials such as activated carbon, silica or alumina.

In the hydrogenation reactor 73 the hydrogenation of all supplied aromatics to the corresponding cycloparaffins is effected with hydrogen, which is supplied via conduit 74, at temperatures between 100 and 250° C. and at pressures between 1 and 40 bar, absolute. At the outlet of the hydrogenation reactor non-converted hydrogen is separated in a manner known per se and recirculated to the reactor inlet of the hydrogenation reactor by means of a return conduit (not shown). Since this hydrogen stream also contains formed light gases such as methane, a partial stream also must again be removed from the circuit at this point via a non-illustrated conduit (purge).

Furthermore, a part of the hydrogenation product is recirculated to the reactor inlet of the hydrogenation reactor via a further non-illustrated return conduit. In this way, the increase in temperature in the hydrogenation reactor due to the strongly exothermal hydrogenation reactions is limited effectively. The ratio between the recirculated hydrogenated product and the non-hydrogenated alkyl aromatics lies between 1 kg/kg and 10 kg/kg. Due to the recirculation, the molar excess of hydrogen during the hydrogenation lies between 200 and 5000% of the quantity theoretically necessary for the complete saturation of all contained double and aromatic bonds.

To ensure an advantageous configuration of the process in energetic terms, the hydrogenation reactor 73 is operated at approximately the same temperature as the bottom of the column 66, whereby an otherwise necessary heat exchanger between these two plant sections can be omitted, whereby the investment and operating costs of the process are reduced and the economy is improved.

Via conduit 75, the non-recirculated fraction of the hydrogenation product is discharged from the hydrogenation reactor and via conduits 50, 51, 52 and 6 recirculated to the olefin synthesis reactor 7 in which the at least partial conversion of the cycloparaffins to olefins, in particular to propylene, is effected.

The process shown in FIG. 2 has the advantage that the core system of a usual MTP process as shown in FIG. 1 remains the same and substantially need not newly be designed in terms of engineering. Furthermore, in particular the $C_5/C_6$ olefins and also the aromatics are utilized better for the conversion to propylene, and they do not get lost via the MTP gasoline or a purge stream like in the process according to FIG. 1. As a result, the quantity of the original MTP gasoline is reduced distinctly and the propylene yield of the entire process is increased.

Numerical Example

In simulated calculations, which depict the MTP process according to the prior art, the following composition was determined for the material stream in conduit 49:
Conduit 49:

| | |
|---|---|
| $C_5$ olefins: | 4.0 g/h |
| $C_6$ olefins: | 3.1 g/h |
| Sum | 7.1 g/h |

At the same time, the following composition was determined for the material stream in conduit 47:
Conduit 47:

| | |
|---|---|
| Toluene: | 3.0 g/h |
| Xylenes: | 15.0 g/h |
| Sum | 18.0 g/h |

The propylene product stream (corresponding to conduit 25) was 258.8 g/h.

According to the prior art, the olefins in conduit 49 are withdrawn from the process unused via the purge; due to the alkylation according to the invention, they can however be recovered and recirculated. In the above example, the material stream in conduit 49 contains 94 mmol of olefins and the material stream in conduit 47 contains 174 mmol of aromatics, which corresponds to a molar ratio of 1.85.

The alkylation reactor 63 accordingly is charged with 25.1 g/h of feed via stream 47 and 49. The paraffin fraction is not taken into account, as the paraffins show an inert behavior.

On the assumption that 80% are alkylated in a targeted way, an alkylation product (conduit 69) of 13.7 g/h and non-converted aromatics (stream 68) of 10.0 g/h are obtained. The non-converted olefins (1.4 g/h) are still withdrawn from the plant via conduit 70.

Via conduit 72, a stream of 23.7 g/h then is supplied to the hydrogenation reactor 73, to which then after complete hydrogenation of alkylate and aromatics a hydrogenated product (stream 75) of 24.7 g/h is recirculated into the reactor 7 via conduit 50.

In a simplified way it can then be assumed that under reaction conditions the alkylation products are split again, wherein olefins (about 5.7 g/h) and cyclohexane derivatives (about 19.1 g/h) are obtained. By converting these components in the reactor 7, about 8.5 g/h more of propylene are obtained (as compared to 258.8 g/h for the process according to the prior art).

By converting these streams to alkyl aromatics and by recirculating the same to the olefin synthesis reactor, the propylene yield could be increased by about 3%.

INDUSTRIAL APPLICABILITY

With the invention an improvement of the MTP process is provided, which allows to at least partly convert the $C_5/C_6$ olefins otherwise admixed to the gasoline product or withdrawn from the process via purge streams and a part of the aromatic products into the target product propylene. At the same time, the quantity of the MTP gasoline obtained as coupling product is reduced, whose further processing and marketing possibly is expensive.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

LIST OF REFERENCE NUMERALS 1, 2 conduit
3 DME reactor
4-6 conduit
7 olefin synthesis reactor
8 conduit
9 cooler
10 conduit
11 compressor
12, 13 conduit
14 distillation column
15 conduit
20 conduit
21 distillation column
22, 23 conduit
24 distillation column
25, 26 conduit
30 conduit
31 separator
32 conduit
33 column
34-36 conduit
40-42 conduit
43 distillation column
44, 45 conduit
46 distillation column
47-53 conduit
49a conduit
60 extractive distillation column
61-63 conduit
64 alkylation reactor
65 conduit
66 distillation column
67-72 conduit
73 hydrogenation reactor
74, 75 conduit

The invention claimed is:
1. A process for producing olefins, in particular propylene, from oxygenates, comprising the following steps:
  (a) heterogeneously catalyzed converting of an educt mixture comprising steam and oxygenates under oxygenate conversion conditions in an olefin synthesis reactor to a primary product containing propylene, other olefins, paraffins and aromatics;
  (b) separating the primary product by means of physical separation processes into a $C_{5-}$ fraction, a $C_{5+}$ fraction and an aqueous phase containing non-converted oxygenates;
  (c) separating the $C_{5-}$ fraction by multistage distillation, wherein a propylene product stream and several olefin-containing hydrocarbon fractions are obtained, wherein the several olefin-containing hydrocarbon fractions are at least partly recirculated to the olefin synthesis reactor;
  (d) separating the non-converted oxygenates from the aqueous phase by means of a thermal separation process, recirculation of the separated, non-converted oxygenates and at least a part of the water to the olefin synthesis reactor;
  (e) separating the $C_{5+}$ fraction by multistage distillation, wherein a $C_{7-}$ fraction is obtained which comprises $C_5/C_6$ olefins, and wherein a $C_{7+}$ fraction is obtained which comprises aromatics;
  (f) separating the $C_{7+}$ fraction by a thermal separation process into an aromatics fraction and a fraction comprising the $C_{7+}$ paraffins;
  (g) supplying at least a part of the $C_{7-}$ fraction comprising the $C_5/C_6$ olefins and at least a part of the aromatics fraction to an alkylation reactor in which by heterogeneously catalyzed conversion of the aromatics with the

$C_5/C_6$ olefins on an alkylation catalyst under alkylation conditions an alkylation product is obtained, which comprises alkyl aromatics;

(h) separating the alkylation product by a thermal separation process in a stream containing $C_5/C_6$ paraffins, an alkyl aromatics stream and a stream containing non-converted aromatics, which is at least partly recirculated to the alkylation reactor;

(i) supplying the alkyl aromatics stream to a hydrogenation reactor having a hydrogen catalyst effective for heterogeneously converting the alkyl aromatics to produce a hydrogenation product comprising cycloparaffins; and (j) recirculating at least a part of the hydrogenation product to the olefin synthesis reactor.

2. The process according to claim 1, wherein the hydrogenation hydrogen is used as a hydrogenating agent.

3. The process according to claim 1, wherein the hydrogenation is carried out such that parts of the product stream of the hydrogenation are recirculated into the hydrogenation, and that the ratio between the recirculated hydrogenated product and non-hydrogenated alkyl aromatics lies between 1 kg/kg and 10 kg/kg.

4. The process according to claim 1, wherein after step (i) hydrogen is separated and recirculated to the hydrogenation reactor, wherein the molar excess of hydrogen during the hydrogenation lies between 200 and 5000% of the quantity theoretically necessary for the complete saturation of all contained double and aromatic bonds.

5. The process according to claim 1, wherein process step (a) is effected in two stages, wherein in the first stage methanol is converted into dimethyl ether and in the second stage dimethyl ether is converted to a primary product containing propylene, other olefins, paraffins and aromatics, and wherein methanol is recirculated to before the first stage and/or water is recirculated in the form of steam to before the second stage.

6. The process according to claim 1, wherein at least a part of the $C_{7-}$ fraction obtained in process step (e), which comprises the $C_5/C_6$ olefins, is recirculated to the olefin synthesis reactor.

7. The process according to claim 1, wherein at least a part of the stream obtained in process step (h), which contains non-converted aromatics, is supplied to the hydrogenation reactor.

8. The process according to claim 1, wherein in the olefin synthesis reactor and in the alkylation reactor the same catalyst is used.

9. The process according to claim 1, wherein in process step (g) the ratio of the sum of the moles of aromatics in the aromatics-containing streams or fractions to the sum of the moles of olefins in the $C_{7-}$ fraction supplied to the alkylation reactor lies between 1 and 10 mol/mol.

10. The process according to claim 1, wherein in process step (g) the ratio of the sum of the moles of aromatics in the aromatics-containing streams or fractions to the sum of the moles of olefins in the $C_{7-}$ fraction supplied to the alkylation reactor lies between 1 and 5 mol/mol.

11. The process according to claim 1, wherein in process step (g) the ratio of the sum of the moles of aromatics in the aromatics-containing streams or fractions to the sum of the moles of olefins in the $C_{7-}$ fraction supplied to the alkylation reactor lies between 1 and 2 mol/mol.

12. A plant for producing olefins from oxygenates, in particular for carrying out the process according to any of the preceding claims, comprising the following plant sections which are in fluid connection with each other:

at least one olefin synthesis reactor for the heterogeneously catalyzed conversion of at least one oxygenate to a primary product containing propylene, other olefins, paraffins and aromatics;

a first separating device configured to separate the primary product into a $C_{5-}$ fraction, a $C_{5+}$ fraction and an aqueous phase containing non-converted oxygenates;

a second separating device configured to separate the $C_{5-}$ fraction into a propylene product stream and several olefin-containing hydrocarbon fractions, as well as second return conduits for recirculating at least a part of the olefin-containing hydrocarbon fractions to the olefin synthesis reactor;

a third separating device configured to separate the non-converted oxygenates from the aqueous phase, as well as third return conduits for recirculating at least a part of the non-converted oxygenates and at least a part of the water to the olefin synthesis reactor;

a fourth separating device configured to separate the $C_{5+}$ fraction into a $C_{7-}$ fraction which comprises $C_5/C_6$ olefins, and into a $C_{7+}$ fraction which comprises aromatics;

a fifth separating device configured to separate the $C_{7+}$ fraction into an aromatics fraction and a fraction comprising the $C_{7+}$ paraffins;

an alkylation reactor for the heterogeneously catalyzed conversion of aromatics with $C_5/C_6$ olefins to an alkylation product which comprises alkyl aromatics, as well as first conduits for supplying at least a part of the $C_{7-}$ fraction comprising the $C_5/C_6$ olefins and at least a part of the aromatics fraction to the alkylation reactor;

a sixth separating device for separating the alkylation product into a stream containing $C_5/C_6$ paraffins, an alkyl aromatics stream and a stream containing non-converted aromatics, as well as a sixth return conduit for recirculating at least a part of the stream containing non-converted aromatics to the alkylation reactor;

a hydrogenation reactor for hydrogenating the alkyl aromatics to a hydrogenation product which comprises cycloparaffins; and a hydrogenation product return conduit configured to recirculate at least a part of the hydrogenation product to the olefin synthesis reactor.

13. The plant according to claim 12, further comprising a $C_{7-}$ fraction return conduit configured to recirculate at least a part of the $C_{7-}$ fraction comprising the $C_5/C_6$ olefins to the olefin synthesis reactor.

14. The plant according to claim 12, further comprising a non-converted aromatics conduit configured to supply at least a part of the stream containing the non-converted aromatics to the hydrogenation reactor.

* * * * *